United States Patent [19]

Yen

[11] 4,125,531
[45] Nov. 14, 1978

[54] 2-SUBSTITUTED-1-AZABICYCLO[2.2.2]OC-TANES

[75] Inventor: Chung H. Yen, Skokie, Ill.
[73] Assignee: G. D. Searle & Co., Chicago, Ill.
[21] Appl. No.: 788,189
[22] Filed: Apr. 18, 1977
[51] Int. Cl.² .......................................... C07D 453/02
[52] U.S. Cl. .................................. 546/133; 424/267;
546/137; 542/455; 542/434
[58] Field of Search ...................................... 260/293.53
[56] References Cited
U.S. PATENT DOCUMENTS 3,506,672  4/1970  Warawa et al. .................. 260/293.53
4,013,667  3/1977  Yen .................................. 260/293.53

FOREIGN PATENT DOCUMENTS 2,502,916  9/1975  Fed. Rep. of Germany ...... 260/293.53

*Primary Examiner*—Henry R. Jiles
*Assistant Examiner*—Richard A. Schwartz
*Attorney, Agent, or Firm*—Joy A. Serauskas

[57] ABSTRACT

This invention encompasses novel 2-(2,2-diphenyl-4-pentenyl-1-azabicyclo[2.2.2]octane and related compounds. These compounds are useful anti-diarrheal agents which possess little if any analgesic activity.

15 Claims, No Drawings

2-SUBSTITUTED-1-AZABICYCLO[2.2.2]OCTANES

The present invention addresses itself to 2-(2,2-diphenyl-4-pentenyl-1-azabicyclo[2.2.2]octane and related compounds thereof. Specifically this invention addresses itself to compounds of the general formula

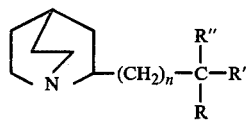

(I)

and pharmaceutically acceptable acid addition salts thereof wherein R and R' are independently selected from the group consisting of phenyl, pyridyl, monosubstituted halophenyl, monosubstituted alkylphenyl wherein the alkyl radical contains 1 to 4 carbon atoms; R" is selected from the group consisting of an alkyl radical containing 1 to 8 carbon atoms, alkenyl radical containing 3 to 6 carbon atoms, cycloalkyl radical containing 3 to 6 carbon atoms, cycloalkyl alkyl radical wherein the first alkyl contains 3 to 6 carbon atoms and the second alkyl contains 1 to 3 carbon atoms, and cycloalkenyl radical containing 4 to 7 carbon atoms and $n$ is a positive integer of 1 to 3.

The halo atoms encompassed by formula (I) include fluoro, chloro, bromo and iodo atoms. The alkyl radicals are exemplified by methyl, ethyl, propyl, butyl, pentyl, hexyl, heptyl, octyl and the corresponding branched chain isomers thereof. The alkenyl radicals encompassed by formula (I) are exemplified by butenyl, propenyl, pentenyl, hexenyl and the corresponding branched chain isomers thereof. The cycloalkyl radicals encompassed by formula (I) are exemplified by cyclobutyl, cyclopentyl and cyclohexyl. The cycloalkenyl radicals are examplified by cyclobutenyl, cyclopentenyl and cyclohexenyl.

The point of attachment of the halo or alkyl substituent in the compounds of formula (I) in which R and R' can be monosubstituted halophenyl or monosubstituted alkylphenyl is not critical. Thus the substituent may be in an ortho, meta or para position.

Preferred embodiments of the present invention as set out in formula I in which R and R' are phenyl are those in which R" is an alkyl radical containing 1 to 8 carbon atoms and $n$ is one. Specifically 2-(2,2-diphenylpentyl)-1-azabicyclo[2.2.2]octane, 2-(2,2-diphenylhexyl)-1-azabicyclo[2.2.2]octane, 2-(2,2-diphenylpropyl)-1-azabicyclo[2.2.2]octane, 2-(2,2-diphenyloctyl)-1-azabicyclo[2.2.2]octane and 2-(2,2-diphenylheptyl)-1-azabicyclo[2.2.2]octane are preferred.

Preferred embodiments of the present invention as set out in formula I in which R and R' are phenyl are those in which R" is an alkenyl radical containing 3 to 6 carbon atoms and n is one. Specifically 2-(2,2-diphenylpent-4-enyl)-1-azabicyclo[2.2.2]octane and 2-(5-methyl-2,2-diphenylhex-4-enyl)-1-azabicyclo[2.2.2]octane are preferred.

Preferred embodiments of the present invention as set out in formula I in which R and R' are phenyl are those in which R" is an cycloalkyl radical containing 3 to 6 carbon atoms and $n$ is one. Specifically 2-(2-cyclopentyl-2,2-diphenylethyl)-1-azabicyclo[2.2.2]octane(Z)-2-butenedioate(1:1) and 2-(2-cyclohexyl-2,2-diphenylethyl)-1-azabicyclo[2.2.2]octane are preferred.

Preferred embodiments of the present invention as set out in formula I in which R and R' are phenyl are those in which R" is an cycloalkenyl radical containing 3 to 6 carbon atoms and $n$ is one. Specifically 2-(2-cyclohexenyl-2,2-diphenylethyl)-1-azabicyclo[2.2.2]octane is preferred.

Equivalent to the organic bases of this invention are non-toxic, pharmaceutically acceptable acid-addition salts which are formed by the addition of a variety of organic acids and inorganic acids to the free base. Such salts are formed with acids such as sulfuric, phosphoric, hydrochloric, hydrobromic, hydroiodic, sulfamic, citric, lactic, maleic, malic, succinic, tartaric, cinnamic, acetic, benzoic, gluconic, ascorbic and related acids.

The compounds of the present invention are useful in consequence of their valuable pharmacological properties. They are, for example, potent anti-diarrheal agents as evidenced by their ability to inhibit gastronintestinal motility as set out in the following tests:

Mouse Cecal Test

The method used for this assay is a modification of the techniques previously described by Macht and BarbaGose, J. Amer. Pharm. Ass., 20, 558 (1931), and Janssen and Jageneau, J. Pharm. Pharmacol., 9, 381 (1957). Details are as follows:

A group of six, male Charles River mice weighing 20–25 g. which have been previously fasted for 24 hours are pretreated with the test compounds administered orally as a solution in water or suspended in 0.5% methyl cellulose. A constant volume of 10 ml./kg. is employed. Thirty minutes following administration of the test compounds, the animals are given a single oral dose of charcoal which consists of 0.2 ml. per mouse of 10% charcoal suspended in 1.0% methyl cellulose. Three and a half hours after charcoal administration, the animals are sacrificed and the cecum examined for the absence or presence of charcoal on an all-or-none basis.

The median effective dose ($ED_{50}$) is then calculated for each compound using the logistic method of Berkson (1953).

The median effective dose ± standard Error $ED_{50}$ ± SE) for the following representative compounds of the present invention in the Mouse Cecal Test are

| | $ED_{50}$ ± S.E. mg/kg, IG |
|---|---|
| 2-(2,2-diphenyloctyl)-1-azabicyclo[2.2.2]octane maleate | 20.67 ± 12.3 |
| 2-(2,2-diphenylheptyl)-1-azabicyclo[2.2.2]octane maleate | 5.84 ± 1.94 |
| 2-(2,2-diphenylhexyl)-1-azabicyclo[2.2.2]octane | 8.74 ± 3.95 |
| 2-(2,2-diphenylpropyl)-1-azabicyclo[2.2.2]octane | 43.10 ± 15.54 |
| 2-(5-methyl-2,2-diphenylhex-4-enyl)-1-azabicyclo[2.2.2]octane | 1.45 ± 0.66 |
| 2-(2,2-diphenyl-4-pentenyl)-1-azabicyclo[2.2.2]octane | 1.82 ± 0.45 |
| Diphenoxylate . HCl (standard) | 3.12 ± 1.29 |

Castor Oil-Induced Diarrhea in the Rat

Adult Charles River male rats are fasted in community cages for 24 hours prior to the test, with free access to water. The test compound is then administered intragastrically (suspended on 0.5% methyl cellulose) one hour prior to the intragastric adminstration of a dose of 1.0 ml. castor oil per rat. The rats are then observed for the presence or absence of diarrhea at hourly intervals for up to 8 hours past the castor oil adminstration. Using the method of Berkson (1953), the median effective dose ($ED_{50}$) values are calculated at each hourly interval for the test compound.

The median effective dose at 2 hours past the castor oil adminstration for the following representative compounds of the present invention in the castor oil-induced diarrhea in the Rat test are:

|  | $ED_{50} \pm S.E.$ mg/kg. IG |
|---|---|
| 2-(2,2-diphenylheptyl)-1-azabicyclo[2.2.2]octane maleate | 10.18 ± 1.43 |
| 2-(2,2-diphenylhexyl)-1-azabicyclo[2.2.2]octane | 4.57 ± 0.21 |
| 2-(5-methyl-2,2-diphenylhex-4-enyl)-1-azabicyclo[2.2.2]octane | 1.74 ± 0.53 |
| 2-(2,2-diphenyl-4-pentenyl)-1-azabicyclo[2.2.2]octane | 1.13 ± 0.18 |

The compounds of this invention advantageously demonstrate little or no analgesic activity at the test doses. The assessment of this activity is conducted by the following assay

Tail Clip Test

A special clip is applied to the base of the tail of the mouse and the time for the animal to turn around to bite at it is measured. The sensitivity of each mouse is determined one-half hour prior to drug adminstration. Only those mice attempting to bite the clip are included in the experiment. The test compound is then adminstered and the response to placement of the clip is determined at 30, 60, 90 and 120 minutes after treatment. A response is considered positive if the animal takes more than 2 times the pre-drug time to bite at the clip at any of these time intervals. A test compound is considered active when 50 percent or more of the animals used show a positive response.

Mouse Hot Plate Test

A mouse is placed in a restraining cylinder on a hot plate with the temperature controlled at 55 ± 0.3° C. The reaction time of the mouse to lick a foot or jump is measured at 60, 40, and 20 minutes before, and 30, 60, 90 and 120 minutes after administration of the test compound. The "normal" reaction time is measured as the median of the three pretreatment reaction times. A positive response consists of a reaction time greater than twice the normal time at any of the post-treatment times. A dose of test compound is considered active when 50 percent or more of the animals used show a positive response.

Compounds of the present invention are conveniently prepared according to the procedure illustrated by Scheme A wherein R and R' are independently selected from the group consisting of phenyl, pyridyl, monosubstituted halophenyl, monosubstituted alkylphenyl wherein the alkyl radical contains 1 to 4 carbon atoms; R" is selected from the group consisting of an alkyl radical containing 1 to 8 carbon atoms, alkenyl radical containing 3 to 6 carbon atoms, cyclaolkyl radical containing 3 to 6 carbon atoms and cycloalkenyl radical containing 4 to 7 carbon atoms and X is chloro or bromo.

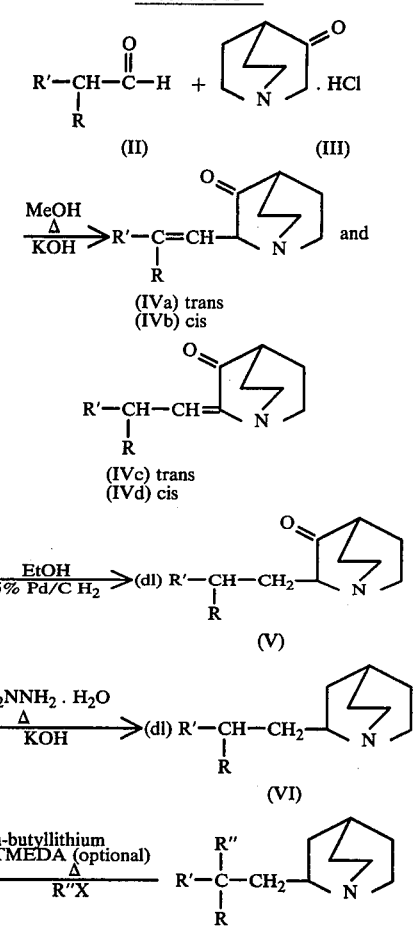

By way of the illustration, the first step of Scheme A is shown by the condensation of diphenylacetaldehyde with 1-azabicyclo[2.2.2]octan-3-one. This reaction is conveniently conducted in an organic solvent, a particularly preferred solvent being methanol. This reaction produces a mixture of isomers illustrated by formulas IVa-IVd which when subjected to catalytic hydrogenation, produce the 2-(2,2-diarylethyl)-1-azabicyclo[2.2.2]octan-3-ones of formula (V).

The oxo group of the compounds of formula (V) is then reduced using a hydrazine hydrate and a base according to the Wolff-Kishner method.

The resulting compounds of formula (VI) are then treated with butyl lithium in the presence of or absence of N,N,N',N'-tetramethylethylenediamine and compounds of the general formula R"-X in which R" and X are defined as above to afford the compounds of formula I.

Scheme A illustrates the preparation of compounds of the general formula I wherein R, R' and R" are defined as before and n is one. It would be obvious to one skilled in the art that Scheme A would also serve to illustrate the preparation of compounds of formula I in which n could be a positive integer of 2 or 3 by beginning with the appropriate starting material in order to obtain the desired compounds.

The following examples describe in detail the preparation of compounds of the present invention. It will be apparent to those skilled in the art that many modifications both of materials and method, may be practiced without departing from the purpose and intent of this disclosure. Throughout the examples hereinafter set forth, temperatures are given in degrees Centigrade (° C.) and relative amounts in parts by weight, except as otherwise noted.

EXAMPLE 1

64.8 Parts of 1-azabicyclo[2.2.2]octan-3-one hydrochloride and 100 parts of diphenylacetaldehyde are suspended in 600 parts by volume of methanol and heated to boiling to form a solution. Then 40.0 parts of potassium hydroxide in 200 parts by volume of hot methanol is added with stirring. The hot solution is filtered and the solid which is collected is rinsed with 100 parts by volume of methanol. The filtrate is diluted with 1000 parts by volume of toluene. This mixture is distilled until 1660 parts by volume of distillate is collected and a head temperature of 110° C. is reached. The pot residue is then diluted with 500 parts by volume of xylene, heated to reflux under a Dean-Stark collector for 40 minutes, cooled to room temperature, and the brown gum is removed by filtration. The filtrate is decanted from the gummy precipitate which forms during standing, washed with water and dried over anhydrous sodium sulfate. Removal of the solvent under reduced pressure affords an oily residue which is dissolved in 180 parts by volume of ethyl ether. The vessel containing the solution is then scratched to induce crystallization. The resulting crystals are filtered, washed with ethyl ether and air-dried to give a first crop melting at 141°–149° C. Reducing the volume of the mother liquor to 100 parts by volume, diluting the liquor with 15 parts by volume of n-pentane and cooling the liquor provide a second crop of crystals, melting at 110°–111° C. Both crops of crystals are mixtures containing various amounts of the two isomers (cis and trans of 2-(2,2-diphenylethylidenyl)-1-azabicyclo[2.2.2]octan-3-one) and 2-(2,2-diphenylethenyl)-1-azabicyclo[2.2.2]octan-3-one.

EXAMPLE 2

25.7 Parts of a mixture of the isomers (cis and trans) of 2-(2,2-diphenylethylidenyl)-1-azabicyclo[2.2.2]octan-3-one, and 2-(2,2-diphenylethenyl)-1-azabicyclo[2.2.2]octan-3-one is dissolved in 1000 parts by volume of ethanol. Then 5 parts of 5% palladium-on-carbon is added and the mixture is hydrogenated using a Parr low-pressure hydrogenator, at room temperature and a pressure of 60–30 psi for 4 hours. After the hydrogenation is completed the catalyst is removed by filtration. The solution is then stripped in vacuum to give a solid. The solid is dissolved in 500 parts by volume of hot ethyl ether. The solution is filtered and then concentrated on a steam bath to a volume of about 150 parts by volume. The concentrated solution is cooled in an icebath to afford a precipitate which is filtered off from the solvent, washed with cold ethyl ether and dried in vacuo to provide a white solid. This solid is recrystallized from ethyl ether to afford 2-(2,2-diphenylethyl)-1-azabicyclo[2.2.2]octan-3-one melting at 103°–107° C. This compound is represented by the following structural formula

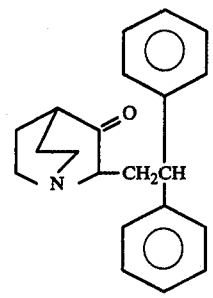

EXAMPLE 3

9.3 Parts of 2-(2,2-diphenylethyl-1-azabicyclo[2.2.2]octan-3-one, 1.3 parts of potassium hydroxide, 3.6 parts by volume of an 85% solution of hydrazine in water and 59 parts diethylene glycol are refluxed together, with stirring, under nitrogen for 2.75 hours. Stirring and heating are then discontinued and the reaction mixture is allowed to stand overnight. The mixture is then heated to distill under nitrogen until a head temperature of 235° C. is reached. After cooling to room temperature, the mixture is partitioned between 900 parts by volume of 5% sodium chloride solution and two 600 parts by volume portions of ethyl ether. The ethereal extracts are combined, washed with water, dried over anhydrous sodium sulfate and stripped in vacuo to give an residual oil which solidifies upon standing. This solid is dissolved in 300 parts by volume of hot n-pentane. The solution is then concentrated on the steam bath to 45 parts by volume and cooled to room temperature to give a solid precipitate which is filtered off, washed with n-pentane and dried in vacuo to give a white solid 2-(2,2-diphenylethyl)-1-azabicyclo[2.2.2]octane, melting at about 87.5°–89° C. This compound is represented by the following structural formula

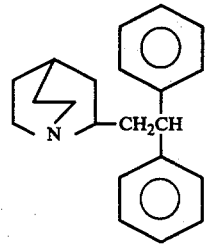

The white solid is dissolved in 100 parts by volume of dry ethyl ether and treated with an excess of a solution of hydrogen chloride in isopropanol. The gum which precipitates solidifies and is filtered off and washed with ethyl ether. Recrystallization from a mixture of ethanol and ethyl ether affords 2-(2,2-diphenylethyl)-1-azabicyclo[2.2.2]octane hydrochloride, melting at about 218° C.–221° C. This compound is represented by the following structural formula

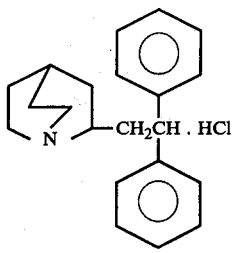

EXAMPLE 4

To a solution of 2.91 parts of 2-(2,2-diphenylethyl)-1-azabicyclo[2.2.2]octane in 40 parts by volume of cyclohexane is added under a nitrogen atmosphere 5.1 parts by volume of a 2.17 M solution of butyl lithium in hexane and 1.15 parts of TMEDA (tetramethylethylenediamine). This solution is then stirred at reflux for 1.25 hour. The resulting brick-red mixture is cooled in an ice-bath. Then 2.01 parts of n-butyl iodide is added and the solution is stirred without cooling for 18 hours. A yellow mixture containing a solid results. The mixture is then washed with 5 portions of water and extracted with dilute hydrochloric acid. This extraction results in the formation of three phases: water, oil and cyclohexane. The cyclohexane phase is siphoned off. The aqueous phase and the oil phase are combined, washed with cyclohexane, treated with excess aqueous sodium hydroxide and extracted with ethyl ether. The ethereal extract is dried over anhydrous sodium sulfate and then stripped in vacuo to give a brown oil. This brown oil is then chromatographed using neutral silica gel as the column adsorbent and a solvent mixture of benzene-ethanolconcentrated ammonium hydroxide (97:3:1/4) as the eluent. The desired fractions are combined and stripped in vacuo to give an oil. This oil is taken up in ethyl ether and extracted with dilute hydrochloric acid. Basifying the acidic extract with aqueous sodium hydroxide liberates an oil.

This oil is then extracted with ethyl ether. The ethereal extract is dried over sodium sulfate and then stripped in vacuo to give an oil. The oil is taken up in n-pentane; this solution is filtered to remove any trace of undissolved material. Evaporation of the filtrate leaves an oil which solidifies upon standing. The solid is dried in vacuo to give a white solid which is 2-(2,2-diphenylhexyl)-1-azabicyclo[2.2.2]octane. This compound melts at about 68°–72° C. and is represented by the following structural formula

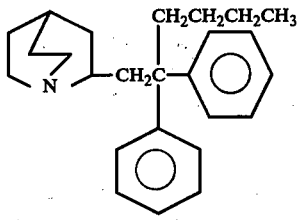

EXAMPLE 5

To a solution of 2.91 parts of 2-(2,2-diphenylethyl)-1-azabicyclo[2.2.2]octane in 40 parts by volume of cyclohexane are added under a nitrogen atmosphere 4.6 parts by volume of a 2.5 M solution of butyl lithium in hexane and 1.5 parts by volume of N,N,N'N'-tetramethylethylenediamine. The mixture is heated to reflux, with stirring, for 1⅝ hour and then cooled to room temperature. 1.45 Parts of 3-bromopropene is then added during a 5-second period. Stirring is continued for about 6 minutes during which time the internal temperature reaches a maximum of 43° C. and then subsides. The resulting yellow mixture is washed with seven portions of water and then extracted with dilute hydrochloride acid. The acidic, aqueous extract is washed with ethyl ether and then basefied with aqueous sodium hydroxide resulting in the liberation of an oil. This oil is then extracted with ethyl ether. The ethereal extract is dried over anhydrous sodium sulfate and stripped in vacuo to give a light brown oil. This oil is crystallized from methanol and water to afford as a white solid, 2-(2,2-diphenyl-4-pentenyl)-1-azabicyclo[2.2.2]octane melting at about 95.5°–98° C. This compound is represented by the following structural formula:

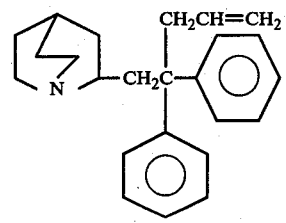

EXAMPLE 6

0.50 Parts of 2-(2,2-diphenyl-4-pentenyl)-1-azabicyclo[2.2.2]octane is dissolved in 50 parts by volume of ethanol. This solution is then added to a Parr hydrogenation bottle which contains 0.05 parts of 5% palladium-on-carbon. The mixture is hydrogenated at room temperature and atmosphere pressure using a 50 ml buret to measure hydrogen uptake. After the hydrogenation is completed the catalyst is removed by filtration. The solution is then stripped in vacuo to afford a gum. Crystallization of this gum from methanol/water affords a white solid which is dried in vacuo at 60° C. for 4 hours to give 2-(2,2-diphenylpentyl)-1-azabicyclo[2.2.2]octane. This compound melts at about 115°–117.5° C. and is represented by the following structural formula

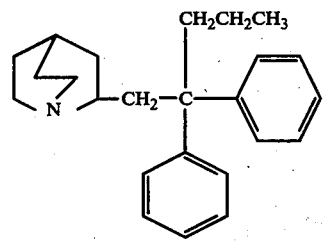

EXAMPLE 7

To a solution of 1.46 parts of 2-(2,2-diphenylethyl)-1-azabicyclo[2.2.2]octane in 20 parts by volume of cyclohexane is added under a nitrogen atmosphere 2.4 parts by volume of 2.5 M solution of butyl lithium. The mixture is heated with stirring at reflux temperature for one hour. After cooling this mixture to 0° C. 0.58 part of iodomethane is added. The reaction mixture is then stirred at room temperature for 18 hours. The resulting yellow mixture which contains a white solid and gum is diluted with 100 parts by volume of ethyl ether and then washed with water. The cyclohexane-ethyl ether layer, excluding the gum, is extracted with dilute hydrochloric acid. The acidic, aqueous extract is basified with aqueous sodium hydroxide resulting in the liberation of an oil. This mixture is then extracted with ether. The ethereal extract is dried over anhydrous sodium sulfate and stripped in vacuo to give an oil which is crude 2-(2,2-diphenylpropyl)-1-azabicyclo[2.2.2]octane. This oil is then dissolved in ethyl ether. Treating this ethereal solution with HCl/isoPrOH solution results in the precipitation of a gum. This gum is rinsed with ethyl ether and then dissolved in acetone. The volume of the acetone solution is concentrated and then cooled to induce crystallization. The resulting crystals are filtered, washed with acetone and dried in vacuo to give 2-(2,2-diphenylpropyl)-1-azabicyclo[2.2.2]octane hydrochloride melting at about 261°–264° C. This compound is represented by the following structural formula

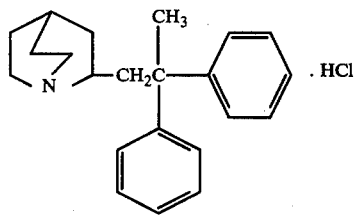

EXAMPLE 8

Following the procedure which is described in Example 4, 2.91 parts of 2-(2,2-diphenylethyl)-1-azabicyclo[2.2.2]octane in 40 parts by volume of cyclohexane, 5.1 parts by volume of a 2.17 M solution of butyl lithium in hexane are reacted with 1.5 parts of TMEDA and 1.81 parts of n-hexyl bromide to provide 2-(2,2-diphenyloctyl)-1-azabicyclo[2.2.2]octane. This compound is then treated with 0.730 parts of maleic acid to give 2-(2,2-diphenyloctyl)-1-azabicyclo[2.2.2]octane maleate, melting at about 180°–181° C. This compound is represented by the following structural formula

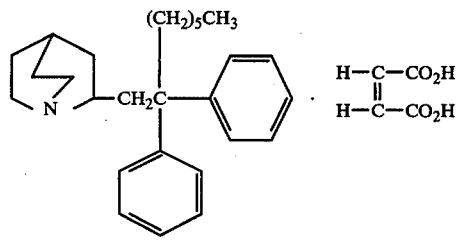

EXAMPLE 9

Following the procedure which is described in Example 4, 2.91 parts of 2-(2,2-diphenylethyl)-1-azabicyclo[2.2.2]octane in 40 parts by volume of cyclohexane, 5.1 parts by volume of a 2.17 M solution of butyl lithium in hexane are reacted with 1.5 parts by volume of TMEDA and 1.65 parts of 1-bromopentane to provide 2-(2,2-diphenylheptyl)-1-azabicyclo[2.2.2]octane. This compound is then treated with 0.570 parts of maleic acid to give 2-(2,2-diphenylheptyl)-1-azabicyclo[2.2.-2]octane maleate, melting at about 177°–178.5° C. This compound is represented by the following structural formula

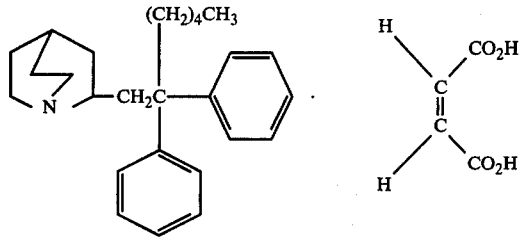

EXAMPLE 10

2.04 Parts of 2-(2,2-diphenylethyl)-1-azabicyclo[2.2.-2]octane and 3.6 parts by volume of a 2.17 M solution of butyl lithium in hexane are dissolved in 30 parts by volume of dry cyclohexane. This solution is refluxed with stirring under a nitrogen atmosphere for 1¾ hours and then cooled in an ice-bath. To this cooled mixture is added, with stirring, 1.16 parts of 1-bromo-3-methyl-2-butene. The cooling bath is removed and the mixture is allowed to stir at ambient temperature for 18 hours. The resulting yellow-colored mixture containing solid is washed with water and then extracted with diluted hydrochloric acid. The acidic aqueous extract is basified with aqueous sodium hydroxide resulting in the liberation of an oil. This oil is then extracted with ethyl ether. The ethereal extract is dried over anhydrous sodium sulfate and stripped in vacuo to give a gum. This gum is then chromatographed using neutral silica gel as the column adsorbent and a solvent mixture of benzene-ethanol-concentrated ammonium hydroxide (98:2:1/2) as the eluent. The desired fractions from the chromatography are combined and stripped in vacuo to leave a residue. This residue is dissolved in n-pentane. The solution is then washed with dilute potassium carbonate, dried over sodium sulfate and evaporated to give an oil which is 2-(5-methyl-2,2-diphenylhex-4-enyl)-1-azabicyclo[2.2.2]octane. This compound is represented by the following structural formula.

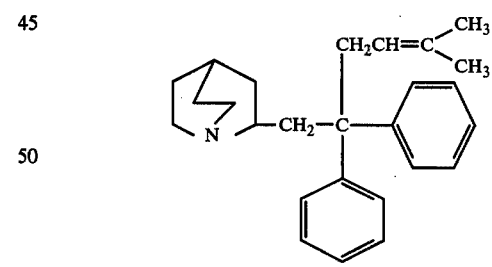

EXAMPLE 11

To a solution of 2.91 parts of 2-(2,2-diphenylethyl)-1-azabicyclo[2.2.2]octane in 40 parts by volume of cyclohexane is added under a nitrogen atmosphere 5.1 parts by volume of 2.17 M solution of butyl lithium in hexane and 1.15 parts of TMEDA. This solution is then stirred at reflux for 1 hour. The resulting brick-red mixture is cooled in an ice-water bath. Then 1.64 parts of bromocyclopentane is added and the solution is stirred for 18 hours at room temperature. After the 18 hour period, a brown-yellow mixture results. This mixture is washed with 7 portions of water and extracted with dilute hydrochloric acid. The acidic extract which contains a small amount of solid is basified with aqueous sodium hydroxide resulting in the formation of a gum. This gum is extracted with ethyl ether. The ether extract is dried over sodium sulfate and then stripped in vacuo to give a gum. The gum is then chromatographed using neutral silica gel as the column absorbent and a solvent mixture of benzene-ethanol-ammonium hydroxide (96:4:1/4) as the eluent. The desired fractions from the chromatography are combined and stripped in vacuo to leave an oil. This oil is dissolved in ethyl ether. The ethereal extract is then extracted with dilute hydrochloric acid. The acidic extract which contains a fine solid is basified with aqueous sodium hydroxide and extracted with ethyl ether. The ethereal extract is washed with sodium chloride, dried over sodium sulfate, and stripped in vacuo to give a gum which is 2-(2-cyclopentyl-2,2-diphenylethyl)-1-azabicyclo[2.2.2]octane. 1.40 Parts of this gum and 0.460 parts of maleic acid are dissolved in 5 parts of methanol. Diluting this solution with 10 parts of ether and seeding result in the formation of crystals. These crystals are then recrystallized from ethyl acetate to give 2-(2-cyclopentyl-2,2-diphenylethyl)-1-azabicyclo[2.2.2]octane (Z)-2-butenedioate (1:1). This compound melts at about 196°–198° C. and is represented by the following formula

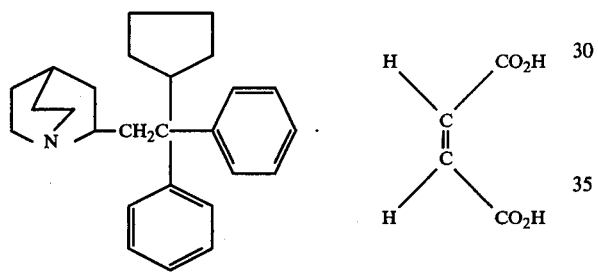

EXAMPLE 12

To a solution of 2.91 parts of 2-(2,2-diphenylethyl)-1-azabicyclo[2.2.2]octane in 40 parts by volume of hexane is added under a nitrogen atmosphere 5.1 parts by volume of 2.17 M solution of butyl lithium in hexane and 1.15 parts of TMEDA. This solution is then stirred at reflux, under nitrogen, for 1 hour. The resulting deep red solution is cooled to room temperature and then placed in an ice-water bath which results in the formation of a red gummy precipitate. To this mixture is now added 1.93 parts of 3-bromocyclohexene. This mixture is now stirred for 25 minutes in a cooling bath. After the 25 minute period, the cooling bath is removed and the mixture is allowed to stir for an additional 10 minutes. The mixture is washed with five portions of water and then extracted with dilute hydrochloric acid which results in the formation of an emulsion; rebasified with aqueous sodium hydroxide. The organic layer is dried over sodium sulfate and stripped in vacuo to give a gum. This gum is taken up in ether. The ethereal extracts are extracted with dilute hydrochloric acid. The acidic extracts are then basified with aqueous sodium hydroxide which results in the formation of an oil. This oil is extracted with ether. These ethereal extracts are washed with water, dried over sodium sulfate and stripped in vacuo to give a gum which contains 2-(2-cyclohexenyl-2,2-diphenylethyl)-1-azabicyclo[2.2.2]octane.

EXAMPLE 13

Substantial repetition of the procedure detailed in Example 11 using an equivalent quantity of cyclohexylbromide for the bromocyclopentane of Example 11 affords 2-(2-cyclohexyl-2,2-diphenylethyl)-1-azabicyclo[2.2.2]octane. Treatment of this material with maleic acid again following the procedure detailed in Example 11 affords 2-(2-cyclohexyl-2,2-diphenylethyl)-1-azabicyclo[2.2.2]octane(Z)-2-butenedioate(1:1) melting at 134.5°–136° C. This compound is represented by the following structural formula

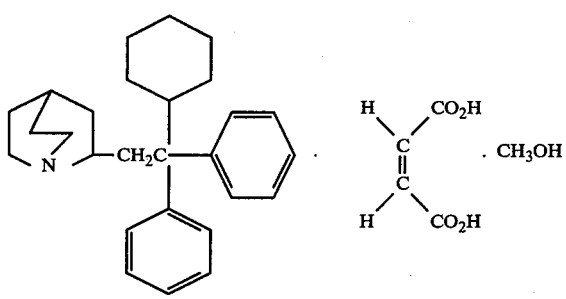

EXAMPLE 14

Repetition of the procedure detailed in Examples 1, 2 and 3 using an equivalent quantity of bis(4-chlorophenyl)acetaldehyde (prepared according to the procedure detailed in J. Med. Chem., 11 (2) 380–382 (1968) in place of the diphenylacetaldehyde affords 2-[2,2-di(4-chlorophenyl)ethyl]-1-azabicyclo[2.2.2]octane.

EXAMPLE 15

Substitution of an equivalent quantity of 2-[2,2-di(4-chlorophenyl)ethyl]-1-azabicyclo[2.2.2]octane in the procedure of Example 4 affords 2-[2,2-di(4-chlorophenyl)hexyl]-1-azabicyclo[2.2.2]octane. This compound is represented by the following structural formula

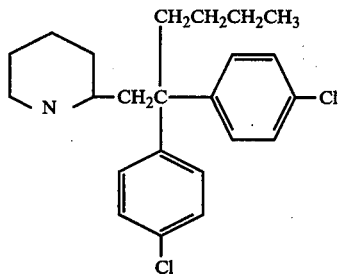

Substitution of an equivalent quantity of 2-[2,2-di(4-chlorophenyl)ethyl]-1-azabicyclo[2.2.2]octane in the procedure of Example 5 affords 2-[2,2-di(4-chlorophenyl)-4-pentenyl]-1-azabicyclo[2.2.2]octane. This compound is represented by the following structural formula

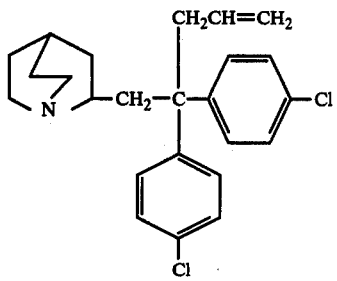

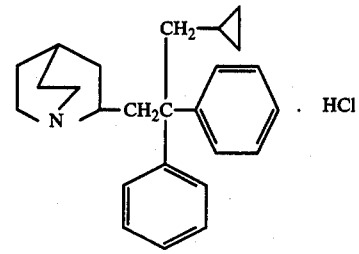

EXAMPLE 16

Repetition of the procedures of Examples 1, 2 and 3 using an equivalent quantity of bis(4-methylphenyl)-acetaldehyde (prepared according to the procedure detailed in U.S.S.R. 173,783, CA64:2005a) in place of the diphenylacetaldehyde affords 2-[2,2-di(4-methylphenyl)ethyl]-1-azabicyclo[2.2.2]octane.

EXAMPLE 17

Substitution of an equivalent quantity of 2[2,2-di(4-methylphenyl)ethyl]-1-azabicyclo[2.2.2]octane for the 2-(2,2-diphenylethyl)-1-azabicyclo[2.2.2]octane of Example 11 and repetition of the procedure which is described in Example 11 affords 2-[2-cyclopentyl-2,2-di(4-methylphenyl)ethyl]-1-azabicyclo[2.2.2]octane.

EXAMPLE 18

To a solution of 1.6 parts of 2-(2,2-diphenylethyl)-1-azabicyclo[2.2.2]octane in 20 parts by volume of cyclohexane are added under a nitrogen atmosphere 2.8 parts by volume of a 2.17 M solution of butyl lithium in hexane and 0.83 parts by volume of N,N,N',N'-tetramethylethylenediamine. Heating this mixture at reflux, with stirring, for one hour under a nitrogen atmosphere results in the formation of a deep red solution. Cooling of this solution in an ice bath results in the formation of a solid. To this mixture is added, dropwise, cyclopropylmethyl bromide. The resulting mixture is stirred at ambient temperature overnight. The mixture is then diluted with 30 parts by volume of cyclohexane, washed with seven portions of water and dried over sodium sulfate. The solution is then stripped in vacuo to give a tan oil. The tan oil is chromatographed using neutral silica gel as the column adsorbent and a solvent mixture of benzene-ethanol-ammonium hydroxide (96:4:1/4) as the eluent. The desired fractions are combined and stripped in vacuo to give a white solid. This solid is then dissolved in ethyl ether and treated with an excess of 7NHCl/isoPrOH which causes the formation of a gummy precipitate. The mixture is stripped in vacuo to give a mixture of solid and gum. This mixture is then triturated with 10 parts of ether until all the gum solidifies. The resulting solid is filtered off, washed with ether and air-dried. The solid is then recrystallized from ethyl acetate to give 2-(2-cyclopropylmethyl-2,2-diphenylethyl)-1-azabicyclo[2.2.2]octane hydrochloride melting at about 224°–226° C. This compound is represented by the following structural formula

EXAMPLE 19

Pharmaceutical formulations are prepared in the following manner with amounts indicating the relative amounts per tablet, capsule, suppository or parenteral product.

TABLET 10 mgs. of a representative compound, e.g. 2-(2,2-diphenyl-4-pentenyl)-1-azabicyclo[2.2.2]octane are dissolved in isopropyl alcohol and distributed on 82.2 mgs. of lactose. The mixture is air-dried and passed through a 40 mesh screen. 24 Mgs. of corn starch and 3.2 mgs. of polyvinylpyrrolidone are added to the drug substance lactose mixture, mixed thoroughly and passed through a 40 mesh screen. The mixture is then granulated with isopropyl alcohol, spread on trays, and dried at 120° F. for 16 hours. The dried granulation is then screened. The granules are mixed thoroughly with 0.6 mgs. of magnesium stearate and the mixture compressed into tablets of the appropriate size. There is thus obtained a tablet having a concentration of active ingredient of 10 mgs.

CAPSULE

10 Mgs. of 2-(2,2-diphenyl-4-pentenyl-1-azabicyclo[2.2.2]octane are mixed thoroughly with 113.75 mgs. of corn starch and 113.75 mgs. of lactose, screened through a 40 mesh screen, and remixed. 12.5 Mgs. of talc are added and the mixture is thoroughly mixed and filled into the appropriate hard gelatin capsule by hand or machine using 250 mgs. fill per capsule. There is thus obtained a capsule having a concentration of active ingredients of 10 mgs.

In the preparation of tablets and capsules from the compounds of the present invention, a variety of excipients can be used. These are summarized as follows: Sugars such as lactose, sucrose, mannitol, or sorbitol; starches such as corn starch, tapioca starch, or potato starch; cellulose derivatives such as sodium carboxymethyl cellulose, ethyl cellulose, or methyl cellulose; gelatin; calcium phosphates such as dicalcium phosphate or tricalcium phosphate; sodium sulfate; calcium sulfate; polyvinylpyrrolidone; polyvinyl alcohol; stearic acid; alkaline earth metal stearates such as magnesium stearate; stearic acid vegetable oils such as peanut oil, cottonseed oil, sesame oil, olive oil, corn oil, surfactants (nonionic, cationic, anionic); ethylene glycol polymers; beta-cyclodextrin; fatty alcohols; hydrolyzed cereal solids; as well as other non-toxic compatible fillers, binders, disintegrants, and lubricants commonly used in pharmaceutical formulations.

PARENTERAL PRODUCTS

1 Mg. of 2-(2,2-diphenyl-4-pentenyl)-1-azabicyclo[2.2.2]octane is dissolved in 0.5 ml of ethanol and 5.0 ml of sesame oil, filtered and filled into an ampul and sealed. The ampul is then sterilized by an appropriate procedure. There is thus obtained an ampul having a concentration of active ingredient, 1 mg/5ml.

In the preparation of parenteral products from the compounds of the present invention a variety of vehicles and solubilizers can be used. These are summarized as follows: vegetable oils such as peanut, corn, cottonseed, sesame oil, benzyl alcohol, saline, phosphate buffer, water, ethylene glycol polymers, urea, dimethylacetamide, triton, dioxolanes, ethyl carbonate, ethyl lactate, glycerol formal, isopropyl myristate, surfactants (nonionic, cationic, anionic), polyalcohols, ethanol.

SUPPOSITORY

990 Mgs. of cocoa butter are melted, preferably on a water or steam bath to avoid local overheating; then 10 mgs. of 2-(2,2-diphenyl-4-pentenyl)-1-azabicyclo[2.2.2]octane is either emulsified or suspended in the melt. Finally, the mass is poured into cooled metal molds, which are chrome plated and the suppository is readily solidified. The total weight of the suppository is 1000 mg.

In the preparation of suppositories from the compounds of the present invention a variety of vehicles and bases for suppository application can be used. These are summarized as follows: triglycerides of oleic, palmitric, and stearic acids (cocoa butter), partially hydrogenated cottonseed oil, branched saturated fatty alcohols such as Suppository base G, Hydrogenated coconut oil triglycerides of $C_{12}$-$C_{18}$ fatty acids, water dispersible vehicles such as the polyethylene glycols, glycerin, gelatin, polyoxyl 40 stearates, and polyethylene-4-sorbitan monostearates, and materials which can raise the melting point of the suppository base, such as beeswax, spermaceti, etc.

What is claimed is:

1. A compound of the formula

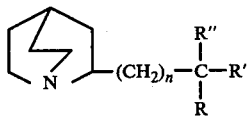

(I)

and pharmaceutically acceptable acid addition salts thereof wherein R and R' are independently selected from the group consisting of phenyl, pyridyl, monosubstituted halophenyl, monosubstituted alkylphenyl wherein the alkyl radical contains 1 to 4 carbon atoms; R" is selected from the group consisting of an alkyl radical containing 1 to 8 carbon atoms, alkenyl radical containing 3 to 6 carbon atoms, cycloalkyl alkyl radical wherein the first alkyl contains 3 to 6 carbon atoms and the second alkyl contains 1 to 3 carbon atoms, and cycloalkenyl radical containing 4 to 7 carbon atoms and $n$ is a positive integer of 1 to 3.

2. A compound according to claim 1 of the formula

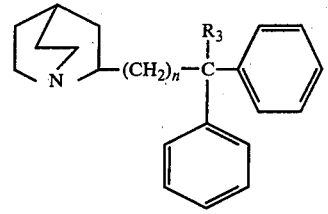

wherein $R_3$ is an alkyl radical containing 1 to 8 carbon atoms and $n$ is a positive integer of 1 to 3.

3. A compound according to claim 1 which is 2-(2,2-diphenyloctyl)-1-azabicyclo[2.2.2]octane.

4. A compound according to claim 1 which is 2-(2,2-diphenylheptyl)-1-azabicyclo[2.2.2]octane.

5. A compound according to claim 1 which is 2-(2,2-diphenylhexyl)-1-azabicyclo[2.2.2]octane.

6. A compound according to claim 1 which is 2-(2,2-diphenylpropyl)-1-azabicyclo[2.2.2]octane.

7. A compound according to claim 1 which is 2-(2,2-diphenylpentyl)-1-azabicyclo[2.2.2]octane.

8. A compound according to claim 1 of the formula

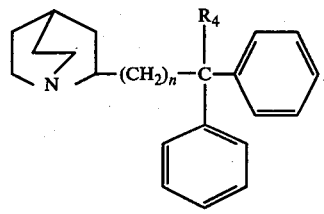

wherein $R_4$ is an alkenyl radical containing 3 to 6 carbon atoms and $n$ is a positive integer of 1 to 3.

9. A compound according to claim 1 which is 2-(2,2-diphenyl-4-pentenyl)-1-azabicyclo[2.2.2]octane.

10. A compound according to claim 1 which is 2-(5-methyl-2,2-diphenylhex-4-enyl)-1-azabicyclo[2.2.2]octane.

11. A compound of the formula

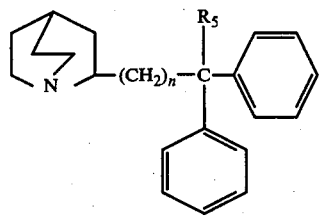

wherein $R_5$ is a cycloalkyl radical containing 3 to 6 carbon atoms and $n$ is a positive integer of 1 to 3.

12. A compound according to claim 11 which is 2-(2-cyclopentyl-2,2-diphenylethyl)-1-azabicyclo[2.2.2]octane.

13. A compound according to claim 11 which is 2-(2-cyclohexyl-2,2-diphenylethyl)-1-azabicyclo[2.2.2]octane.

14. A compound according to claim 1 which is 2-(2-cyclopropylmethyl-2,2-diphenylethyl)-1-azabicyclo[2.2.2]octane.

15. A compound according to claim 1 which is 2-(2-cyclohexenyl)-2,2-diphenylethyl)-1-azabicyclo[2.2.2]octane.

* * * * *